(12) United States Patent
Weill

(10) Patent No.: US 8,317,514 B2
(45) Date of Patent: Nov. 27, 2012

(54) SIMPLIFIED CLEANING AND FILLING DEVICE

(76) Inventor: David Weill, Begnings (CH)

( * ) Notice: Subject to any disclaimer, the term of this patent is extended or adjusted under 35 U.S.C. 154(b) by 475 days.

(21) Appl. No.: 11/629,366

(22) PCT Filed: Jun. 9, 2005

(86) PCT No.: PCT/IB2005/001620
§ 371 (c)(1),
(2), (4) Date: Dec. 11, 2006

(87) PCT Pub. No.: WO2006/008592
PCT Pub. Date: Jan. 26, 2006

(65) Prior Publication Data
US 2007/0287125 A1 Dec. 13, 2007

(30) Foreign Application Priority Data
Jun. 11, 2004 (FR) .................................. 04 06331

(51) Int. Cl.
*A61C 17/00* (2006.01)
*A61C 17/02* (2006.01)
*A61G 17/02* (2006.01)
(52) U.S. Cl. ........................................... 433/80; 433/81
(58) Field of Classification Search .................... 433/80, 433/81, 102; 601/162–165; 422/1, 20, 39, 422/127, 292, 295, 297; 134/184
See application file for complete search history.

(56) References Cited

U.S. PATENT DOCUMENTS
4,021,921 A 5/1977 Detaille
4,671,786 A * 6/1987 Krug .............................. 604/6.1
(Continued)

FOREIGN PATENT DOCUMENTS
EP 0 299 919 A 1/1989
(Continued)

OTHER PUBLICATIONS

Chinese Office Action issued on Jan. 31, 2012 in corresponding Chinese Patent Application No. 200580024162.8.

*Primary Examiner* — Cris L Rodriguez
*Assistant Examiner* — Eric Rosen
(74) *Attorney, Agent, or Firm* — Frommer Lawrence & Haug LLP; Ronald R Santucci

(57) ABSTRACT

Device for difficult intervention in a closed enclosure, including a duct, a first end of which is intended to penetrate within the chamber, the duct being furthermore connected:
  to a pressure reduction device, the function of which is to lower the pressure within the enclosure;
  to an outlet duct for extracting the sucked-up material; and
  to a duct connected to a device for suddenly relieving the pressure and to an opening in the device for bringing the end of the duct into contact with the external air when the pressure within the enclosure reaches a value below a certain threshold.

7 Claims, 4 Drawing Sheets

U.S. PATENT DOCUMENTS

| | | | |
|---|---|---|---|
| 4,993,947 A | 2/1991 | Grosrey | |
| 5,261,365 A | 11/1993 | Edwards | |
| 5,295,828 A | 3/1994 | Grosrey | |
| 5,328,041 A * | 7/1994 | Hook et al. | 215/247 |
| 6,083,195 A * | 7/2000 | Perkins et al. | 604/30 |
| 6,497,572 B2 * | 12/2002 | Hood et al. | 433/81 |
| 6,780,166 B2 * | 8/2004 | Kanda et al. | 604/31 |
| 6,824,751 B2 | 11/2004 | Rossell | |
| 6,997,714 B1 * | 2/2006 | Schoeffel | 433/224 |
| 2002/0018735 A1 * | 2/2002 | Rossell | 422/128 |
| 2002/0072032 A1 * | 6/2002 | Senn et al. | 433/80 |
| 2003/0103855 A1 * | 6/2003 | Kim et al. | 417/501 |

FOREIGN PATENT DOCUMENTS

| | | |
|---|---|---|
| EP | 0 538 200 A | 4/1993 |
| EP | 0 521 119 B | 5/1996 |
| WO | WO 92/12685 | 8/1992 |
| WO | WO 95/35069 | 12/1995 |
| WO | WO 00/45859 | 8/2000 |

* cited by examiner

SIMPLIFIED CLEANING AND FILLING DEVICE

This application is a 371 of PCT/IB2005/001620 filed on Jun. 9, 2005, published on Jan. 26, 2006 under publication number WO 2006/008592 A1 which claims priority benefits from French Patent Application Number 04/06331 filed Jun. 11, 2004.

The invention relates to a method and a device for a filling, cleaning, unblocking-type intervention in a closed or virtually closed enclosure. It is particularly suitable for complex-shaped and/or hard-to-reach cavities. It offers many applications including in construction, chemical or food production installations, medicine and dentistry.

BACKGROUND OF THE INVENTION

To clean a closed enclosure, it is known practice to make two openings in the enclosure in order to cause a fluid, gaseous or liquid, where necessary having chemical cleaning properties, to circulate therein at high pressure. This method rapidly reaches its limits:

- for certain complex shapes of the enclosure, walls remain unreachable by the fluid and uncleaned;
- in addition, simple circulation requires a relatively long cleaning time and generally represents mediocre effectiveness.

To fill an air-filled closed or semi-closed cavity with a liquid or pasty substance, it is known practice to connect a water inlet duct in an opening of the cavity and to provide a discharge of the air, either through a second opening or through the same opening. Such a method is however lengthy if the volume is great. In addition, it does not make it possible to perfectly fill a cavity whose shape is complex, has thin and narrow ramifications, in which air pockets remain trapped.

DESCRIPTION OF THE PRIOR ART

Such a filling solution is described in document EP0538200 in the dental field, for which the closed enclosure is the inside of a tooth that has to be filled with a filler paste. This solution consists in a mechanism for aspirating the volume of the tooth allowing it to be filled at the same time with a paste. Such a method has the disadvantages of a lengthy filling if the volume is great, of not allowing a filling of all the interstices of the cavity and residual air pockets remaining trapped.

A second solution in the dental field is described in document U.S. Pat. No. 4,021,921. This solution consists in inserting a liquid inside a tooth with the aid of a pump pushing the liquid. This solution also provides for the addition of gas bubbles and the use of pressure oscillations combined with periodic pulses, applied via a control of the pump allowing it to carry out repeated start and stop cycles. This solution has the advantage of improving the cleaning and filling effect that would be obtained by a simple circulation of pressurized liquid. However, the proposed device has the disadvantage of being complex, of having a voluminous mechanism and of being difficult to apply and to control due to the particular operation of the pump. Additionally, the solution does not make it possible to fully eliminate all the air pockets from the cavity and its filling and cleaning are insufficient.

A third solution in the dental field is described in document EP0299919. This solution is based, on the one hand, on a pump which makes it possible to create a vacuum in the tooth and on a device with a piston which has the function of inserting into the tooth a pressurized cleaning liquid. This device operates on the basis of the cavitation phenomena, of which the high energy involved makes it possible to resolve the disadvantages of the preceding solutions. However, such a solution requires two controlled pumping systems, relatively long ducts, many connections, depends on the inertia of the components in motion, the inertia of the columns of liquids in motion and is subjected to the various damping factors associated with the various components such as the ducts in the context of the pressure variations. This solution relies therefore on a complex mechanism posing problems of reliability. In addition, the energy consumed is considerable and this solution causes a considerable consumption of liquid. Finally, it generates cavitation phenomena that are always accompanied by often undesirable violent effects and are not suitable for the envisaged uses. A variant of this solution, which has the same disadvantages, is described in document EP0521119.

A solution having similar disadvantages is described in document EP0766535.

Another solution using cavitation is described in document EP1146914. It consists in the creation of a low pressure by a device that is periodically placed in contact with the enclosure to be cleaned, in alternation with a setting at atmospheric pressure. This solution is based on a rotor rotated by a motor and containing several internal ducts to connect the various pressure sources to the cavity of the closed enclosure. This device has many disadvantages like those mentioned previously, to which the fact of using the rotor is added: specifically, this device requires particular connections between the ducts, causes losses of energy and wear by friction, problems of sealing and hygiene because the liquid passes through the rotor.

When a duct is blocked, it is known practice to try to unblock it by filling it, for example with water, according to the preceding technique hoping that the pressure will be sufficient to clear the blockage. In practice, this method is limited in the case of stubborn blockages.

SUMMARY OF THE INVENTION

A general object of the invention consists in proposing a method and a device that allow difficult intervention of the cleaning, filling, unblocking type in a hard-to-reach closed cavity.

More precisely, the object of the invention is to propose a method and a device suitable for filling, cleaning, unblocking-type operations that make it possible to obtain a good result and in a short time.

An object of the invention also consists in proposing a method and a device suited to different fields such as construction, chemical or food installations, the cavity being able to be a liquid-conveying duct or a tank, or such as the medical and dental field, the cavity being able to be an artery or a tooth.

An object of the invention consists in proposing a simple method and device, of little bulk and low cost.

The concept of the invention consists in subjecting the enclosure, within which the intervention is necessary, to cycles of sudden pressure releases, causing a particular motion of fluid, gaseous, liquid and even pasty, within the enclosure, which has the effect of cleaning, filling, unblocking the enclosure.

More precisely, the device according to the invention for difficult intervention in a closed enclosure comprises a duct, a first end of which is intended to penetrate within the enclosure, the duct being furthermore connected:

a) to a pressure reduction means, the function of which is to lower the pressure within the enclosure;

b) to an outlet duct for extracting the sucked-up material; and c) to a duct connected to a device for suddenly relieving the pressure and to an opening in the device for bringing the end of the duct into contact with the external air when the pressure within the enclosure reaches a value below a certain threshold.

The pressure reduction means may be employed by an air circulation causing the pressure to be lowered by the Venturi effect.

The device may be connected to a waste extraction duct.

The device may include a ball pushed toward the opening by a spring, so as to bring or not bring the enclosure into contact with the outside via the opening of the device.

The device may comprise a duct, one end of which is designed to penetrate within the enclosure and the other end of which is suitable for connection with another duct connected to a fluid reservoir.

It may comprise an end-fitting made of silicone or elastomer through which the end of the tube or tubes designed to penetrate within the enclosure passes, the silicone end-fitting being adapted to its positioning in an opening of the enclosure.

One of the two ducts passing through the silicone or elastomer end-fitting may protrude by a greater length in order to penetrate more deeply within the enclosure.

This device may be used for dental care. As a variant, it may be used for cleaning objects, such as a contact lens.

The invention also relates to a method for difficult intervention in a closed enclosure comprising the repetition of the following two steps:

the pressure is lowered at the end of a duct connected to the enclosure via its other end; and below a threshold value of the pressure within the enclosure, the contacting of the duct via a duct and an opening with the external air at atmospheric pressure so as to obtain a sudden rise in the pressure within the enclosure.

The method for difficult intervention in a closed enclosure may include a circulation of air within the duct so as to cause the pressure within the duct to be lowered by the Venturi effect.

The method for difficult intervention may include in parallel with the two preceding steps, a step of supplying the enclosure with fluid via a duct.

DESCRIPTION OF THE DRAWINGS

These objects, features and advantages and others of the present invention will be explained in detail in the following description of particular embodiments given on a nonlimiting basis in relation to the appended figures amongst which.

DESCRIPTION OF THE PREFERRED EMBODIMENTS

Figure 1:
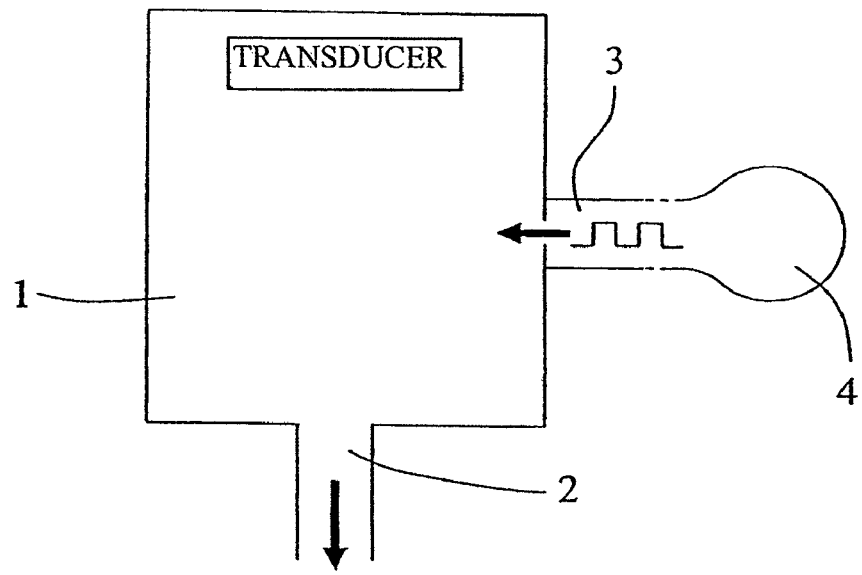
FIG. 1 represents a schematic view illustrating the concept of the invention.
Figure 2:
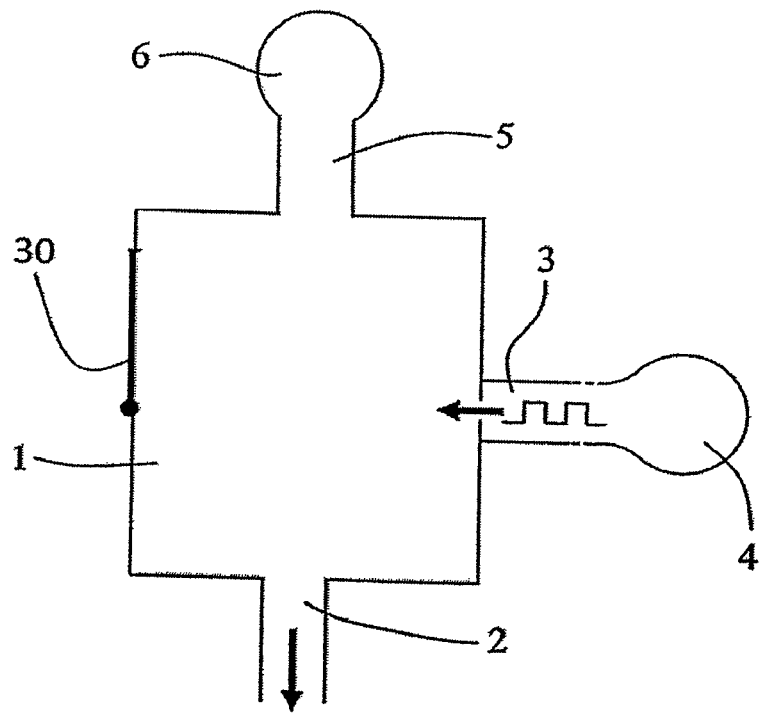
FIG. 2 represents a schematic view of a variant of a device according to the concept of the invention.
Figure 3:
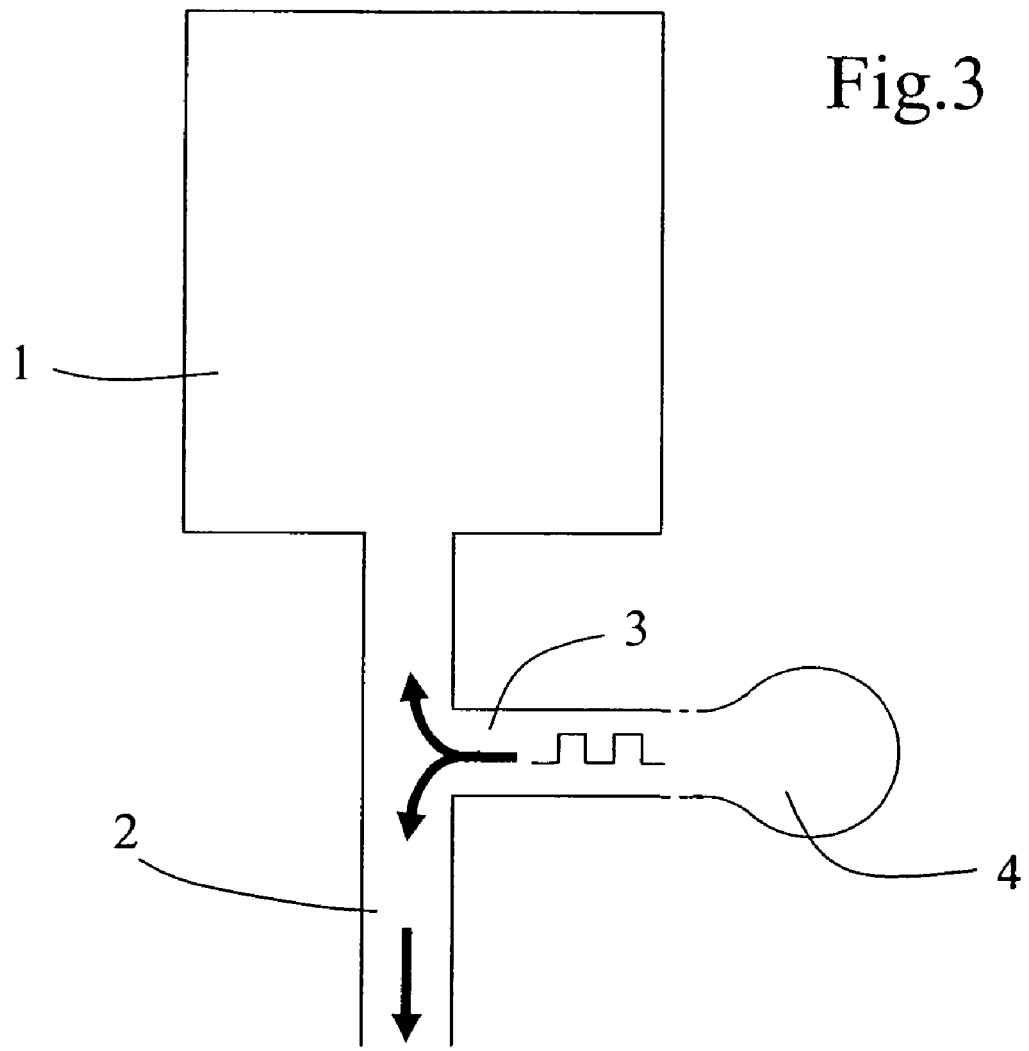
FIG. 3 represents a variant of the diagram of FIG. 1.

FIGS. 1 to 3 represent schematic devices illustrating the concept of the invention.

FIG. 1 illustrates a closed cavity 1 on which it is necessary to intervene, for a cleaning operation. The device according to the invention comprises a pressure reduction means 2 connected to the cavity via a first opening, this means being a pump in this embodiment, a means of sudden pressure release 3 connected to the enclosure 1 via a second opening, this means being a valve-type release device in this embodiment and this means being connected to a reservoir containing a fluid 4, air at atmospheric pressure in this embodiment.

For reasons of simplification, the cavity is represented schematically as rectangular. It could however have any complex form and particularly have hard-to-reach nooks.

The cleaning method of the invention, applied with the aid of the foregoing device, comprises the following essential steps:

reduction of the pressure inside the enclosure 1 with the aid of the suction pump 2 which sucks out the air present in the enclosure;

below a certain threshold pressure, sudden release caused by the valve 3, which consists in the sudden inrush of the air 4 into the enclosure and causes the sudden pressure increase inside the enclosure.

The foregoing steps are repeated cyclically.

The pressure reduction means 2 may be of a mechanical type such as a pump, of the hydraulic type, such as a turbine, of the electromechanical type, such as a vibration pump whose operating cycle is sufficiently high to be considered continuous. It operates in a continuous or virtually continuous manner so that it causes a virtually permanent flow of air within the enclosure.

The release device 3 has the function of causing a sudden pressure increase, and may consist in a simple device suddenly placing the enclosure at low pressure in contact with the outside at constant pressure, such as the air at atmospheric pressure for example. It may consist in a simple mechanical device consisting of a ball, a cylinder or an element of any shape suitable for blocking off an opening of the enclosure and connected to a spring, this element being able to be moved so as to release the opening of the enclosure when the pressure difference between the inside and the outside of the enclosure reaches a sufficient value to oppose the force of the spring. This device may also be based on the constant elasticity of a material that makes it possible to open a valve when the pressure reduction exceeds a certain threshold. This phenomenon causes a sudden change in the virtually permanent flow. As a variant, this device may be controlled, the valve being mechanically controlled for example.

The combination and repetition of the two foregoing effects make it possible to create a circulation of air marked by violent movements inside the enclosure which makes it possible to obtain a better cleaning than with a simple flow.

This device may also be used with any fluid 4. Note that in the case of a liquid such as water, by nature incompressible, such a device remains effective by the fact that there always remain at least a few air bubbles within the enclosure, a phenomenon due to the imperfect geometry of the walls of the enclosure, to the possible presence of solid or liquid contaminants, and possible imperfect sealing of the enclosure, at the openings for example, which allows the device to produce the pressure cycle described hereinabove. According to the concept of the invention, the extreme conditions of cavitation are not sought and are not necessary, unlike the prior art. However, the invention remains compatible with these extreme conditions and nothing would prevent the device from operating in such conditions if certain applications required it.

FIG. 2 represents a schematic view of a variant embodiment. In this variant, the device includes additionally a means 5 of supplying a fluid 6, water in this embodiment, through a third opening in the enclosure 1. The supply means may be a simple duct connected to a water reservoir at a certain pressure, advantageously high and constant.

This device makes it possible to carry out the following steps:
- reduction of the air pressure inside the enclosure 1 with the aid of the suction pump 2 which sucks out the air present in the enclosure;
- in parallel, filling of the enclosure with the water originating from the supply means 5, this filling being promoted by the pressure of the water at the inlet and by the suction via the means 2;
- below a certain threshold pressure, sudden release caused by the valve 3, which consists in the sudden inrush of the air 4 into the enclosure and causes the sudden pressure increase inside the enclosure.

Note that this device makes it possible to obtain the following effects:
- the release of air inside the enclosure creates an impact inside the enclosure, that is transmitted into the volume of the enclosure by the water due to its virtually incompressible character;
- without any particular priming method, the enclosure finishes by being filled with water, this filling being better than in the case of a simple supply of water.

Specifically, this device makes it possible to reach any corners of the enclosure, under the effect of the sudden releases;
- nevertheless, there always remain a few gas bubbles which allow the suction then release mechanism to continue operating even when the enclosure is almost entirely full of water. These air bubbles are of very small size and often invisible to the naked eye at atmospheric pressure. They may move at random with the sudden convection movements generated by the releases and they have a volume which increases with the pressure reduction, this volume variation also being able to be an additional source of convection movement in the liquid. Thanks to these phenomena, the gas bubbles actively participate in the cleaning of the surfaces;
- the cleaning effect within the enclosure is very effective.

Finally, this device makes it possible to combine the action of two complementary fluids, the air which allows a mechanism of pressure reduction then sudden release, and the water, with, where necessary, an addition of liquid cleaning product, which may have a more effective cleaning effect than the air alone, and participates effectively in the transmission of the shock waves. Naturally, any other combination of fluids, liquid, gaseous and even pasty, is possible, as is the use of a liquid comprising solid particles in suspension.

This device and method therefore make it possible to obtain improved cleaning. It is possible to exploit the principles of the invention in a secondary application to clean an object that is positioned in the enclosure.

In addition, they make it possible to fill the enclosure 1 well with water. Finally, this system is also perfectly suited to the unblocking of the enclosure, due to the fact that filling is improved and makes it possible to reach zones that are difficult to reach with a simple flow, and due to the fact that the sudden pressure reductions make it possible to transfer impacts that have a positive effect on the unblocking action.

FIG. 3 represents schematically a variant of the device of FIG. 1, which has the advantage of requiring only a single opening in the enclosure 1 to use the functions of pressure reduction and sudden pressure release. Specifically, in this case, the pressure release device 3, in the form of a valve, is connected to an opening of the outlet duct of the pressure reduction mechanism.

Figure 4:
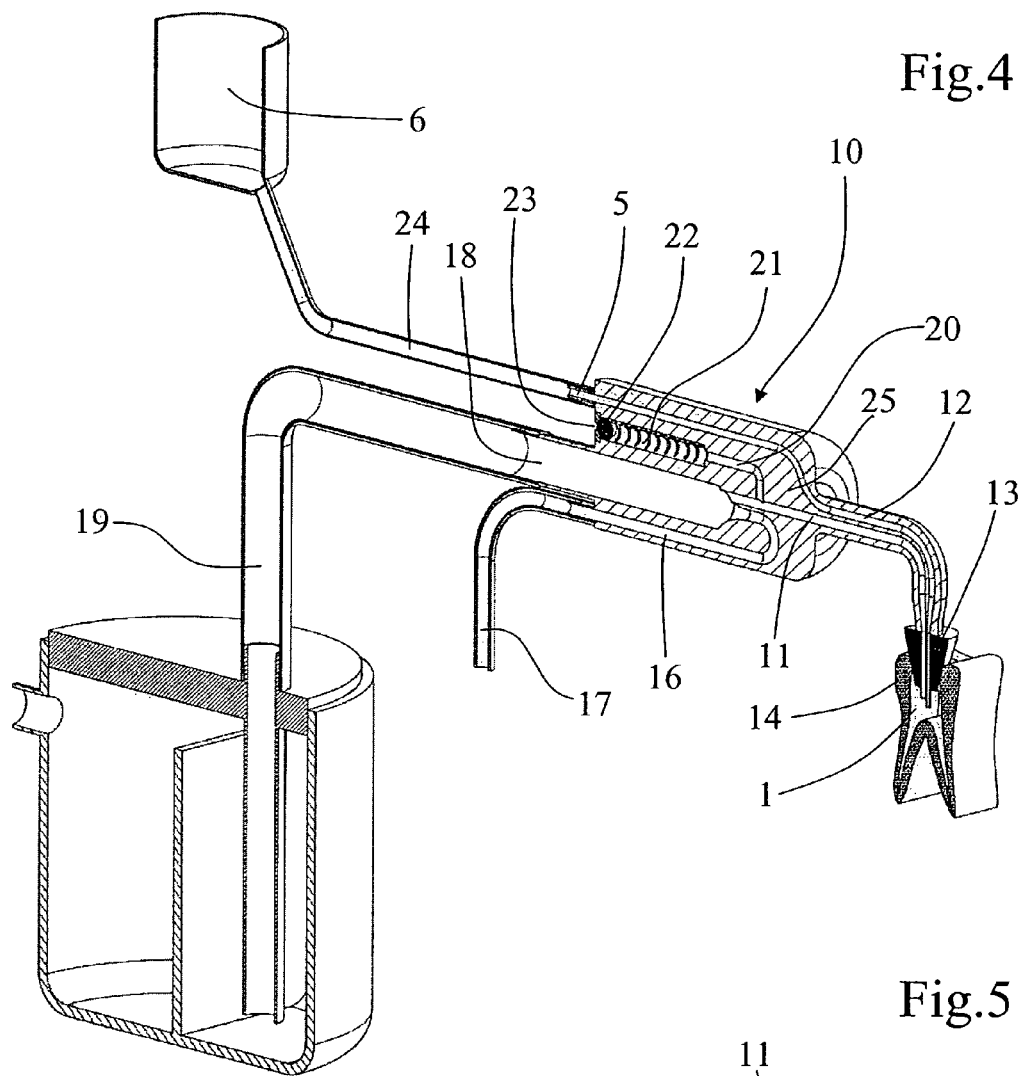
FIG. 4 represents a perspective view of a device according to the invention in a dental application.

FIG. 4 shows a particular device 10 suitable for dental care.

Figure 5:
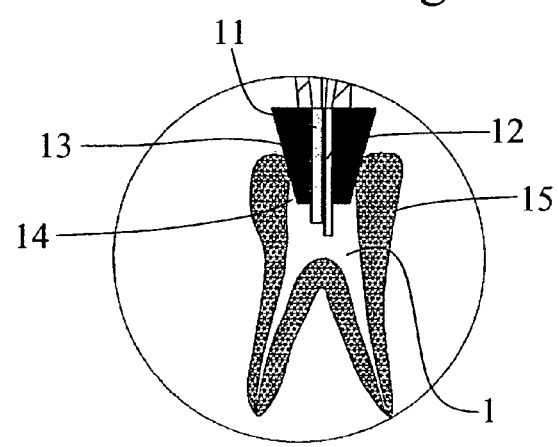
FIG. 5 shows a detailed view of the device of FIG. 4.

As shown in FIG. 5, this device comprises two ducts 11 and 12 passing through a frustoconical silicone end-fitting 13 placed in an opening 14 in a tooth 15 so as to penetrate into the tooth cavity 1. The duct 11 participates in the pressure-reducing function, while the duct 12 is a fluid supply duct 6. Advantageously, the supply duct 12 penetrates further so as to avoid potential interaction between the two ducts (11 and 12) which would for example run the risk of causing direction suction of the fluid 6 via the duct 11 immediately on it exiting from the duct 12. The plug 13 is a simple silicone plug pushed right into an opening 14 in the tooth, which plug is in particular held in place in operating mode by the low pressure within the cavity 1.

The device 10 further includes a duct 16 that can be connected to an external air circulation duct 17, such as those available in hospitals. This duct 16 joins the end of the duct 11 to a larger-diameter outlet duct 18. This construction makes it possible for the duct 16 to cause a pressure reduction at the end of the duct 11 by the Venturi effect. This geometry is designed to allow the device to operate over a pressure range. The duct 11 and the duct 16 therefore fulfill the pressure reduction function 2, as illustrated in FIGS. 1 to 3. As a variant, another pressure reduction means could be used at the end of the duct 11, such as a suction pump.

The materials extracted via the duct 11 are guided by the duct 18, which may be connected to a duct 19 leading to a hygienic waste collection device. Moreover, a duct 20 is connected, on one side, to the duct 11 and, on the other side, to a system consisting of a ball 22 and a spring 21, the operation of which was described above. When the pressure reaches a sufficiently low value, the spring 21 is compressed under the pressure of the external air, which ends up suddenly penetrating into the duct 20 via the opening 23 and then into the cavity 1 of the tooth via the duct 11, causing a sudden rise in pressure. The ball 22 is then again pushed back by the spring 21 so as to block the opening toward the outside. This assembly, composed of the duct 20, the ball 21, the spring 22 and the opening 23, fulfils the function of suddenly releasing the pressure. The duct 12 is connected at its end to a duct 24 connected to a reservoir containing the fluid 6. This assembly represents the feed device 5.

This device 10 includes a shell 25 so as to contain and protect the various ducts. This shell has an outlet intended for the tooth and, more precisely, the two ends of the ducts 11 and 12. This shell includes four other connections to the outside, in order to allow the ducts 16, 18, 12, 20 as described above to be connected.

This device makes it possible, on the one hand, to clean the cavity 1 of the tooth with the aid of a cleaning fluid 6. It also makes it possible to fill this cavity with a paste, by putting it in the place of the cleaning fluid.

Figure 6:
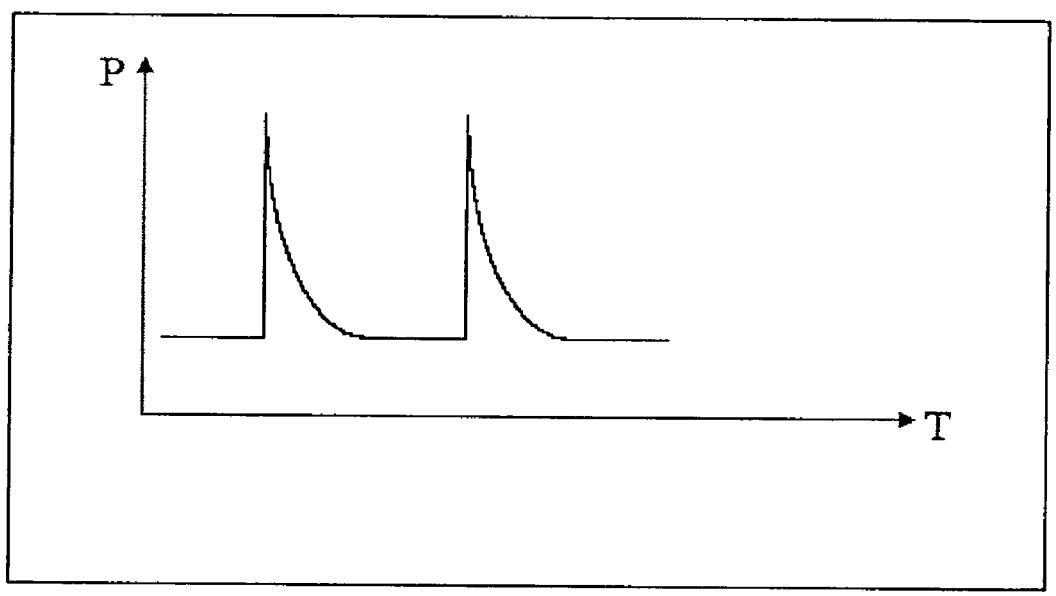
FIG. 6 represents the pressure curve as a function of the time obtained with the device of FIG. 4.

This device makes it possible to achieve the pressure curve shown in FIG. 6 within the cavity of the tooth 1. In a first phase, the pressure drops continuously then, in a second phase, the pressure suddenly rises again, that is to say in a very short time, to atmospheric pressure.

Those skilled in the art will adapt the device to suit it to the different fields of application mentioned hereinabove.

As an additional comment, this device can function in other particular conditions in which there is a change of state of a fluid, in which there are cavitation phenomena. It remains compatible with the addition of complementary components such as pressure sensors, devices such as a transducer 7 in contact with the fluid or submerged in the cavity (FIG. 1) in order to add complementary vibratory and/or thermal phenomena, of the ultrasound type for example.

The device and method of the invention finally have the following advantages:
- it is suitable for various fields of application, being applied to small volumes just as well as to industrial installations several cubic meters in volume;
- it makes it possible to achieve very good cleaning, filling, unblocking performance in a short time;
- it is highly simplified, low cost, can be discarded after one use, which is very advantageous in, for example, the medical and dental fields whose requirements in terms of hygiene are very considerable;
- it is not very bulky and can be very easily connected to external ducts, to a cavity to be treated;
- the material sucked out does not pass through all the main functions of the device, but is directed toward a waste collector;
- it operates with only a simple supply of gas and, where necessary, a supply of fluid. It does not require a large amount of energy; and
- it is primed only by its filling properties.

The invention claimed is:

1. A device for difficult intervention in a closed enclosure (1), comprising
    a first duct (11), a first end of which is intended to penetrate into the enclosure (1), wherein the first duct (11) is furthermore connected:
        to a pressure reduction means adapted to suck out air present in the closed enclosure and lower the pressure within the enclosure (1) to a pressure less than the pressure outside the closed enclosure;
        to an outlet duct (18) for extracting a sucked-up material from the closed enclosure; and
        to a duct (20) connected to a pressure relieving device (21, 22), the pressure relieving device having an opening (23) in contact with external air, such that, when the difference in pressure between the inside of the enclosure (1) and the external air reaches a sufficient value, external air suddenly penetrates into the closed enclosure (1) via the duct (20) and the first duct (11), causing a sudden rise in pressure inside the enclosure;
    a second duct (12), one end of which is designed to penetrate within the enclosure (1) and the other end of which is suitable for connection with a duct (24) connected to a fluid reservoir (6); and
    an end-fitting (13) made of silicone or elastomer through which the end of the first and second ducts (11; 12) designed to penetrate into the enclosure (1) passes, the end-fitting being adapted to its positioning in an opening (14) of the enclosure (1).

2. The device as claimed in claim 1, wherein the first duct (11) is connected at its end to a duct (16) having an end suitable for connection with an air circulation duct (17) so as to lower the pressure in the enclosure (1) by the Venturi effect.

3. The device as claimed in claim 1, wherein the outlet duct (18) has an end suitable for connection with a waste extraction duct (19).

4. The device as claimed in claim 1, wherein the pressure relieving device includes a ball (22) thrust toward the opening (23) of the pressure relieving device by a spring (21), so as to bring or not bring the end of the duct (20) connected to the pressure reliving device into contact with the external air via the opening (23).

5. The device as claimed in claim 1, wherein one of the first and second ducts (11, 12) protrudes by a greater length from the end-fitting (13) in order to penetrate more deeply within the enclosure (1).

6. The device as claimed in claim 1, which is a device for dental care.

7. The device as claimed in claim 1, which further includes a transducer in order to add at least one of vibratory, thermal, and ultrasound phenomena within the enclosure (1).

* * * * *